United States Patent
Okazaki et al.

(10) Patent No.: US 9,739,748 B2
(45) Date of Patent: Aug. 22, 2017

(54) GAS SENSOR AND GAS DETECTION ELEMENT

(71) Applicant: NGK SPARK PLUG CO., LTD., Nagoya-shi, Aichi (JP)

(72) Inventors: Satoshi Okazaki, Kasugai (JP); Seiji Oya, Niwa-gun (JP); Yuta Oishi, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 223 days.

(21) Appl. No.: 14/664,408

(22) Filed: Mar. 20, 2015

(65) Prior Publication Data

US 2015/0276658 A1    Oct. 1, 2015

(30) Foreign Application Priority Data

Mar. 26, 2014  (JP) .................................. 2014-063684
Jan. 21, 2015  (JP) .................................. 2015-009505

(51) Int. Cl.
*G01N 27/407*    (2006.01)

(52) U.S. Cl.
CPC .............................. *G01N 27/4071* (2013.01)

(58) Field of Classification Search
CPC ........................................ G01N 27/407–27/41
See application file for complete search history.

(56) References Cited

U.S. PATENT DOCUMENTS

| | | | | |
|---|---|---|---|---|
| 4,310,401 | A * | 1/1982 | Stahl | G01N 27/4071 204/426 |
| 7,083,710 | B2 | 8/2006 | Scheer et al. | |
| 2002/0003088 | A1* | 1/2002 | Ozawa | G01N 27/4077 204/424 |
| 2003/0089603 | A1 | 5/2003 | Scheer et al. | |
| 2010/0155240 | A1* | 6/2010 | Matsuoka | G01N 27/4077 204/424 |

FOREIGN PATENT DOCUMENTS

JP    4813729 B2    9/2001

* cited by examiner

*Primary Examiner* — J. Christopher Ball
(74) *Attorney, Agent, or Firm* — Stites & Harbison, PLLC; Jeffrey A. Haeberlin; Joseph P. Morris (57) ABSTRACT

A gas detection element of a gas sensor has a reference gas introduction passage formed therein and extending from an opening at a radially outer perimetric surface of an element rear-end portion to a detecting section of an element forward-end portion for introducing reference gas from the opening to the detecting section. The entirety of the reference gas introduction passage is provided on a forward side in an axial direction with respect to contact portions of electrode pads and through hole conductors which are formed on and in the element rear-end portion.

8 Claims, 7 Drawing Sheets

GAS SENSOR AND GAS DETECTION ELEMENT

BACKGROUND OF THE INVENTION

Field of the Invention

The present invention relates to a gas sensor which includes a tubular metallic shell having an axial hole, and a plate-like gas detection element inserted into the axial hole and held to the metallic shell and which detects a particular gas component contained in gas to be measured, and to a gas detection element for use in the gas sensor.

Description of Related Art

Conventionally, there is a gas sensor disposed in, for example, an exhaust pipe of an internal combustion engine and adapted to detect a particular gas component contained in gas to be measured, such as an oxygen sensor for detecting the oxygen concentration of exhaust gas. A known gas sensor of this type includes a tubular metallic shell having an axial hole, a single or a plurality of holding members disposed in the axial hole, and a plate-like gas detection element which is held to the metallic shell through the holding member(s).

The gas detection element has a detecting section provided at an element forward-end portion located forward of the holding members, and adapted to detect a particular gas component contained in gas to be measured. The gas detection element also has electrode pads provided on an element rear-end portion located rearward of the holding members; furthermore, in some cases, the gas detection element has through hole conductors provided in the element rear-end portion and electrically communicating with the electrode pads, respectively. Terminal members come into contact with the respective electrode pads on the element rear-end portion. Also, a certain detection element is configured such that the element rear-end portion is exposed to a reference gas space (for example, a space filled with reference gas, such as the air), and configured to have a reference gas introduction passage formed therein and extending from an opening formed at the element rear-end portion to the detecting section for introducing reference gas to the detecting section from the reference gas space. For example, Patent Document 1 discloses a gas sensor having such a gas detection element (refer to FIGS. 1 to 3 and description associated therewith in Patent Document 1).

RELATED ART DOCUMENTS

Patent Document 1 is Japanese Patent No. 4813729.

SUMMARY OF THE INVENTION

As mentioned above, since the terminal members are in contact with the respective electrode pads of the gas detection element, that region of the element rear-end portion of the gas detection element where contact portions of the electrode pads are formed is required to have a particularly high strength. Also, since that region of the element rear-end portion of the gas detection element where through hole conductors are formed has holes in which the through hole conductors exist, the region is smaller in cross-sectional area than the other region and is thus apt to reduce in strength. Thus, if the reference gas introduction passage is provided in those regions of the element rear-end portion of the gas detection element where the contact portions of the electrode pads and the through hole conductors are provided, the regions further reduce in cross-sectional area and thus unfavorably reduce in strength.

The present invention has been conceived in view of such current situation, and an object of the invention is to provide a gas sensor in which, in spite of provision of a reference gas introduction passage in an element rear-end portion of a gas detection element, deterioration in strength is prevented for those regions of the element rear-end portion where through hole conductors and contact portions of electrode pads in contact with terminal members are provided, as well as a gas detection element for use in the gas sensor.

One mode of the present invention for solving the above problem provides a gas sensor comprising a tubular metallic shell, a holding member, a gas detection element, and a terminal member. The metallic shell has an axial hole extending therethrough in an axial direction. The holding member is disposed in the axial hole of the metallic shell. The gas detection element has a plate-like form extending in the axial direction, is held in the axial hole of the metallic shell through (or by) the holding member, and has an element forward-end portion and an element rear-end portion. The element forward-end portion is located on a forward side in the axial direction with respect to the holding member and includes a detecting section for detecting a particular gas component contained in gas to be measured. The element rear-end portion is located on a rear side in the axial direction with respect to the holding member, is exposed to reference gas, and includes an electrode pad provided on a surface thereof and a through hole conductor provided therein and electrically communicating (i.e., in electrical communication) with the electrode pad. The terminal member is in contact with a contact portion of the electrode pad of the gas detection element. In the gas sensor, the gas detection element has a reference gas introduction passage formed therein and extending from an opening at a radially outer perimetric surface of the element rear-end portion to the detecting section (i.e., the gas detection element defines a reference gas introduction passage extending from the opening to the detecting section) for introducing the reference gas from the opening to the detecting section. The entirety of the reference gas introduction passage is provided on the forward side in the axial direction with respect to the through hole conductor and the contact portion of the electrode pad.

In this gas sensor, the entirety of the reference gas introduction passage is provided on the forward side with respect to the through hole conductor and that contact portion of the electrode pad with which the terminal member is in contact. Thus, reference gas can be reliably introduced to the detecting section. Additionally, there can be prevented deterioration in strength of that region of the element rear-end portion in which the through hole conductor and the contact portion of the electrode pad are provided, which could otherwise result from existence of the reference gas introduction passage.

Notably, the "reference gas introduction passage" is a reference gas flow passage extending in the interior of the gas detection element from the opening at the radially outer perimetric surface of the element rear-end portion (a surface which partially constitutes the element rear-end portion and faces radially outward in relation to the axial line) to the detecting section located at the element forward-end portion. The number of the "reference gas introduction passages" may be one or more than one. Also, the number of the "openings" may be one or more than one. A single reference gas introduction passage may extend from a single opening, or a plurality of reference gas introduction passages may extend from a single opening. Also, reference gas introduction passages extending from respective openings may merge into a single extending reference gas introduction passage. The "reference gas introduction passage" can assume a form of branching off halfway between the opening and the detecting section and extending to the detecting section or may assume a form of merging together halfway between the opening and the detecting section and extending to the detecting section. The "opening" can be provided at one of two main surfaces of the plate-like gas detection element. Also, the "opening" can be provided at a side surface which connects the two main surfaces to each other. As mentioned above, a plurality of "openings" can be provided; for example, the openings can be provided at a main surface and a side surface, respectively, or the openings can be provided at one or more side surfaces.

Also, the "electrode pad," the "terminal member," and the "through hole conductor" may be provided in a quantity of one piece each or of more than one piece each. In the case where the "electrode pad," the "terminal member," and the "through hole conductor" are provided in a quantity of more than one piece each, the entirety of the reference gas introduction passage is provided on the forward side in the axial direction with respect to the through hole conductors and the contact portions of the electrode pads.

Furthermore, preferably, in the gas sensor mentioned above, the entirety of the reference gas introduction passage is provided on the forward side in the axial direction with respect to the electrode pad and the through hole conductor.

In this gas sensor, although the gas detection element has the reference gas introduction passage, that region of the element rear-end portion in which the electrode pad and the through hole conductor are provided can reliably maintain high strength.

Furthermore, preferably, any one of the gas sensors mentioned above further comprises an insulating separator which accommodates the terminal member and partially accommodates the element rear-end portion of the gas detection element. In the gas sensor, the insulating separator is disposed away from the holding member and the metallic shell, and the opening of the reference gas introduction passage is provided on the forward side in the axial direction with respect to the insulating separator.

In this gas sensor, the opening of the reference gas introduction passage is provided on the forward side with respect to the insulating separator, rather than within the insulating separator; i.e., the opening is exposed to a reference gas space filled with reference gas. Thus, reference gas can be more reliably introduced from the opening.

Furthermore, preferably, in any one of the gas sensors mentioned above, the gas detection element has a plurality of ceramic layers laminated in a thickness direction; the radially outer perimetric surface is composed of a pair of main surfaces which face each other in the thickness direction, and side surfaces which connect the two main surfaces to each other; and the reference gas introduction passage is provided along one of the ceramic layers, and the opening is provided at the side surface.

In this gas sensor, the entirety of the reference gas introduction passage is provided along a single ceramic layer which partially constitutes the gas detection element, without extending in the thickness direction of the gas detection element, and the opening is provided at a side surface of the element rear-end portion. In this manner, the reference gas introduction passage assumes a two-dimensionally extending form but not a three-dimensionally extending form, whereby the reference gas introduction passage can be formed easily and reliably; thus, the gas sensors can be manufactured inexpensively with small variations in characteristics.

Another mode of the present invention provides a gas detection element having a plate-like form extending in an axial direction, and comprising an element forward-end portion and an element rear-end portion. The element forward-end portion is located on a forward side in the axial direction and includes a detecting section for detecting a particular gas component in gas to be measured. The element rear-end portion is located on a rear side in the axial direction, has, on a surface thereof, an electrode pad including a contact portion with which a terminal member comes into contact, and has therein a through hole conductor electrically communicating with the electrode pad. The gas detection element has a reference gas introduction passage formed therein and extending from an opening at a radially outer perimetric surface of the element rear-end portion to the detecting section (i.e., the gas detection element defines a reference gas introduction passage which extends from the opening to the detecting section) for introducing reference gas from the opening to the detecting section. In the gas detection element, the entirety of the reference gas introduction passage is provided on the forward side in the axial direction with respect to the through hole conductor and the contact portion of the electrode pad.

In this gas detection element, the entirety of the reference gas introduction passage is provided on the forward side with respect to the through hole conductor and that contact portion of the electrode pad with which the terminal member is in contact. Thus, reference gas can be reliably introduced to the detecting section. Additionally, although the gas detection element has the reference gas introduction passage, there can be prevented deterioration in strength of that region of the element rear-end portion in which the through hole conductor and the contact portion of the electrode pad in contact with the terminal member are provided. Therefore, a gas sensor which uses this gas detection element therein exhibits high reliability.

A further mode of the present invention provides a gas detection element having a plate-like form extending in an axial direction, and comprising an element forward-end portion and an element forward-end portion. The element forward-end portion is located on a forward side in the axial direction and includes a detecting section for detecting a particular gas component in gas to be measured. The element rear-end portion is located on a rear side in the axial direction, has an electrode pad on a surface thereof, and has therein a through hole conductor electrically communicating with the electrode pad. The gas detection element has a reference gas introduction passage formed therein and extending from an opening at a radially outer perimetric surface of the element rear-end portion to the detecting section (i.e., the gas detection element defines a reference gas introduction passage which extends from the opening to the detecting section) for introducing reference gas from the opening to the detecting section. In the gas detection element, the entirety of the reference gas introduction passage is provided on the forward side in the axial direction with respect to the electrode pad and the through hole conductor.

Although this gas detection element has the reference gas introduction passage, that region of the element rear-end portion in which the electrode pad and the through hole conductor are provided can reliably maintain high strength.

Furthermore, preferably, any one of the gas detection elements mentioned above has a plurality of ceramic layers laminated in a thickness direction. In such a gas detection element, the radially outer perimetric surface includes a pair of main surfaces which face each other in the thickness direction, and side surfaces which connect the pair of (i.e., two) main surfaces to each other; and the reference gas introduction passage is provided along one of the ceramic layers, and the opening is provided at one of the side surfaces.

In this gas detection element, the reference gas introduction passage assumes a form of extending two-dimensionally along the ceramic layer rather than three-dimensionally; thus, the reference gas introduction passage can be formed easily and reliably, and the gas detection elements can be manufactured inexpensively with small variations in characteristics.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

A. First Embodiment

Figure 1:
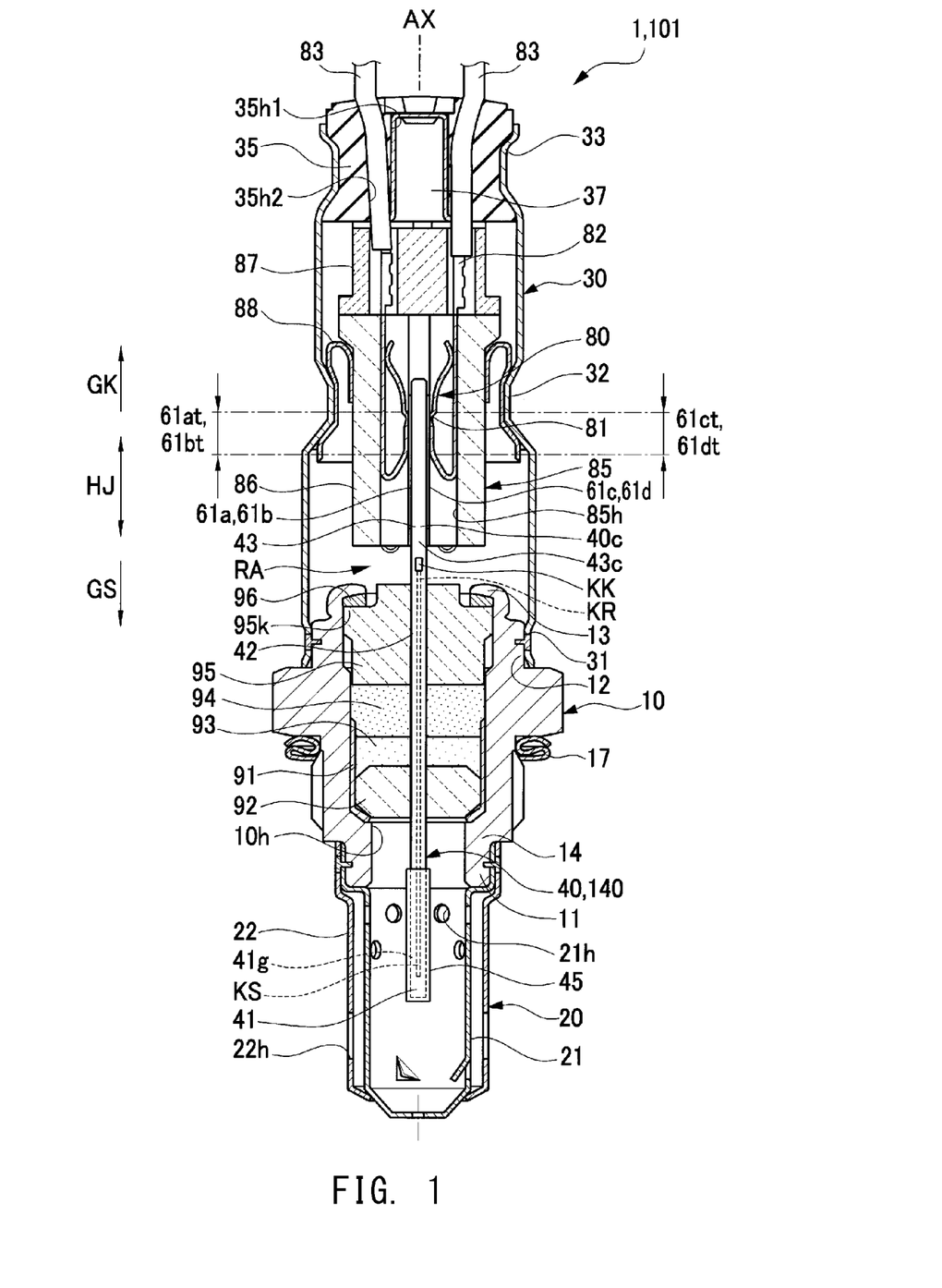
FIG. 1 is a longitudinal sectional view of a gas sensor according to a first embodiment of the present invention.

Embodiments of the present invention will next be described with reference to the drawings. FIG. 1 shows a gas sensor 1 according to a first embodiment. In FIG. 1, a direction along an axial line AX of the gas sensor 1 is referred to as an axial direction HJ. With respect to the axial direction HJ, a side toward a detecting section 41g of a gas detection element 40 (lower side in FIG. 1) is referred to as a forward side GS, and a side opposite the forward side GS (upper side in FIG. 1) is referred to as a rear side GK. This gas sensor 1 is an oxygen sensor and is mounted to an exhaust pipe (not shown) of an automobile; and the detecting section 41g of the gas detection element 40 is exposed to exhaust gas flowing through the exhaust pipe and detects the concentration of oxygen (a particular gas component) contained in exhaust gas (gas to be measured). The gas sensor 1 is composed of a metallic shell 10, a protector 20, an outer tube 30, the gas detection element 40, terminal members 80, an insulating separator 85, holding members 91 to 95, etc.

The metallic shell 10 is a tubular member made of metal (specifically, carbon steel) and having an axial hole 10h extending therethrough in the axial direction HJ. The protector 20, which will be described later, is attached to a metallic-shell forward end portion 11 located at the forward side GS of the metallic shell 10. The outer tube 30, which will be described later, is attached to a rear-end engagement portion 12 located at the rear side GK of the metallic shell 10. Furthermore, a portion of the metallic shell 10 which is located on the rear side GK with respect to the rear-end engagement portion 12 is a crimped portion 13. The crimped portion 13 is formed through radially inward crimping for fixing the gas detection element 40, which will be described later, etc., to the metallic shell 10. Also, an annular gasket 17 is disposed around the outer circumference of the metallic shell 10 in order to prevent leakage of gas from inside the exhaust pipe to which the gas sensor 1 is attached. The metallic shell 10 internally has a stepped portion 14 with which a metal cup 91, which will be described later, is in contact from the rear side GK.

Next, the protector 20 will be described. The protector 20 is a metal member which circumferentially surrounds an element forward-end portion 41 of the gas detection element 40, which will be described later, for protecting the gas detection element 40 from impact caused by adhesion of water. The protector 20 is externally fitted to and joined (specifically, welded) to the metallic-shell forward end portion 11 of the metallic shell 10. The protector 20 has a dual structure consisting of an inner protector 21 which assumes a closed-bottomed tubular form, and a tubular outer protector 22 which radially surrounds the inner protector 21 with a gap formed between the same and the inner protector 21. The inner protector 21 has a plurality of holes 21h formed therein, and the outer protector 22 also has a plurality of holes 22h formed therein.

Next, the outer tube 30 will be described. The outer tube 30 is a tubular metal member extending in the axial direction HJ. A forward end portion 31 of the outer tube 30 is externally fitted and joined (specifically, welded) to the rear-end engagement portion 12 of the metallic shell 10. A central portion, in the axial direction HJ, of the outer tube 30 is crimped radially inward to become a crimped portion 32, thereby pressing a metal holding member 88, which will be described later, radially inward.

An elastic member 35 made of rubber is fitted into a rear end portion 33 of the outer tube 30. The rear end portion 33 is crimped radially inward, thereby fixing the elastic member 35 to the outer tube 30. The elastic member 35 has a first through hole 35h1 formed therein at the center and extending in the axial direction HJ. A filter unit 37 composed of a filter and a metal tubular member for fixing the filter is fitted into the first through hole 35h1. The air is introduced into the outer tube 30 through the filter unit 37. Thus, a space within the outer tube 30 (reference gas space RA) is filled with the air. In the present embodiment, the introduced air corresponds to the aforementioned "reference gas," and the space (reference gas space RA) filled with the air within the outer tube 30 corresponds to the aforementioned "reference gas space."

Also, the elastic member 35 has four second through holes 35h2 (FIG. 1 shows two of them) formed therein around the first through hole 35h1. Lead wires 83, which will be described later, are inserted through the second through holes 35h2, respectively.

As shown in FIG. 1, the tubular metal cup 91 is disposed between the metallic shell 10 and an element trunk portion 42, which will be described later, of the gas detection element 40. The metal cup 91 is in contact with the stepped portion 14 of the metallic shell 10 from the rear side GK. In the metal cup 91, an annular ceramic ring 92 formed of alumina is disposed; an annular first talc ring 93 formed through compressive compaction of talc powder is disposed on the rear side GK of the ceramic ring 92; and the ceramic ring 92 and the first talc ring 93 perimetrically surround the element trunk portion 42.

Furthermore, in the axial hole 10h of the metallic shell 10, an annular second talc ring 94 formed through compressive compaction of talc powder is disposed on the rear side GK of the metal cup 91 and the first talc ring 93; a tubular sleeve 95 formed of ceramic (specifically, alumina) is disposed on the rear side GK of the second talc ring 94; and the second talc ring 94 and the sleeve 95 perimetrically surround the element trunk portion 42. The sleeve 95 has a stepped shoulder portion 95k formed circumferentially at the rear side GK thereof. An annular packing 96 is disposed on the shoulder portion 95k and pressed from the rear side GK as a result of the crimped portion 13 of the metallic shell 10 being formed through crimping. As will be described later, the gas detection element 40 is held to the metallic shell 10 through the metal cup 91, the ceramic ring 92, the first talc ring 93, the second talc ring 94, and the sleeve 95. The metal cup 91, the ceramic ring 92, the first talc ring 93, the second talc ring 94, and the sleeve 95 correspond to the aforementioned "holding member."

Next, the gas detection element 40 will be described. FIGS. 2 to 5 show the gas detection element 40. The gas detection element 40 assumes a slender, rectangular plate-like form extending in the axial direction HJ (longitudinal direction) and has a first main surface 40a and a second main surface 40b in parallel with each other, and a first side surface 40c and a second side surface 40d which connect the first main surface 40a and the second main surface 40b to each other, extend in the axial direction HJ, and are in parallel with each other. In FIG. 1, the gas detection element 40 is illustrated such that the horizontal direction corresponds to the thickness direction thereof.

While being inserted through the axial hole 10h of the metallic shell 10, the gas detection element 40 is held to the metallic shell 10 through the aforementioned holding members 91 to 95. Specifically, the element forward-end portion 41 is located on the forward side GS with respect to the metal cup 91, which is the most forward one among the holding members 91 to 95; an element rear-end portion 43 is located on the rear side GK with respect to the sleeve 95, which is the rearmost one among the holding members 91 to 95; and the element trunk portion 42 located between the element forward-end portion 41 and the element rear-end portion 43 is held to the metallic shell 10 through the holding members 91 to 95.

The element forward-end portion 41 has the detecting section 41g for detecting the concentration of oxygen contained in exhaust gas. The detecting section 41g will be described in detail later. The element forward-end portion 41 is covered with a porous protection layer 45 (see FIG. 1) which contains alumina as a main component. In FIGS. 2 to 5, illustration of the protection layer 45 is omitted.

Figure 5:
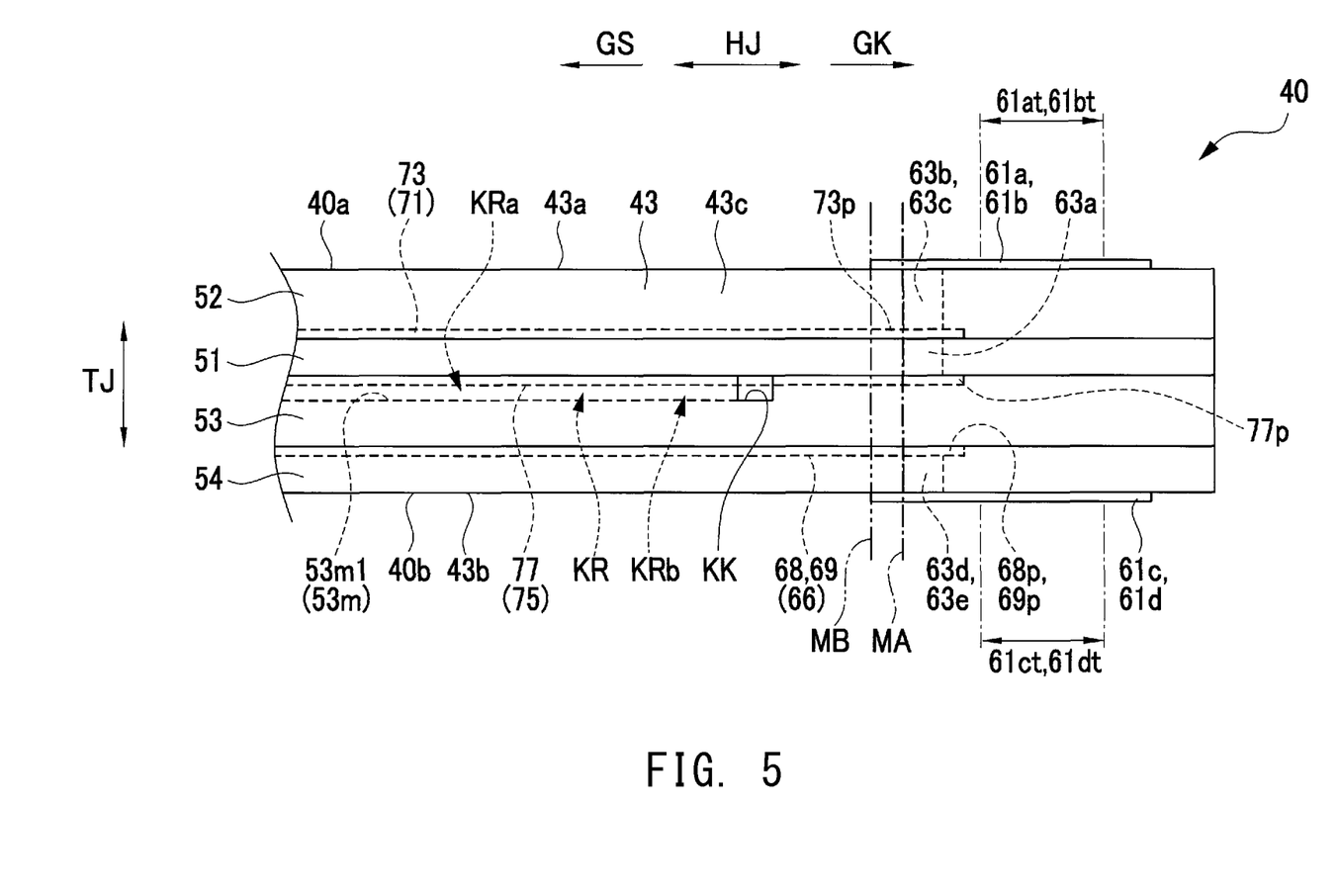
FIG. 5 is a side view of a rear end portion of the gas detection element according to the first embodiment as viewed from a first side surface side.

Meanwhile, the element rear-end portion 43 has a radially outer perimetric surface which faces radially outward in relation to the axial line AX; specifically, a radially outer perimetric surface composed of a first main surface 43a and a second main surface 43b which face each other in a thickness direction TJ, and a first side surface 43c and a second side surface 43d which connect the first main surface 43a and the second main surface 43b to each other, extend in the axial direction HJ, and are in parallel with each other.

Two rectangular electrode pads (a first electrode pad 61a and a second electrode pad 61b) are formed on the first main surface 43a, and two rectangular electrode pads (a third electrode pad 61c and a fourth electrode pad 61d) are formed on the opposite second main surface 43b. As will be described later, in the assembled gas sensor 1, the terminal members 80 are in contact with and electrically connected to the electrode pads 61a to 61d, respectively (see FIG. 1). Those portions of the electrode pads 61a to 61d which the terminal members 80 are in contact with are contact portions 61at, 61bt, 61ct, and 61dt, respectively. As will be described later, the element rear-end portion 43 has a plurality of through hole conductors (a first through hole conductor 63a, a second through hole conductor 63b, a third through hole conductor 63c, a fourth through hole conductor 63d, and a fifth through hole conductor 63e) formed therein in such a manner as to partially extend therethrough.

Also, the gas detection element 40 has a reference gas introduction passage KR formed therein. The reference gas introduction passage KR opens at the first side surface 43c of the element rear-end portion 43 (the reference gas introduction passage KR has an opening KK at the first side surface 43c) and extends through the gas detection element 40 from the opening KK to the detecting section 41g of the element forward-end portion 41 for introducing reference gas contained in the reference gas space RA (specifically, the air introduced into the reference gas space RA) from the opening KK to the detecting section 41g.

Figure 2:
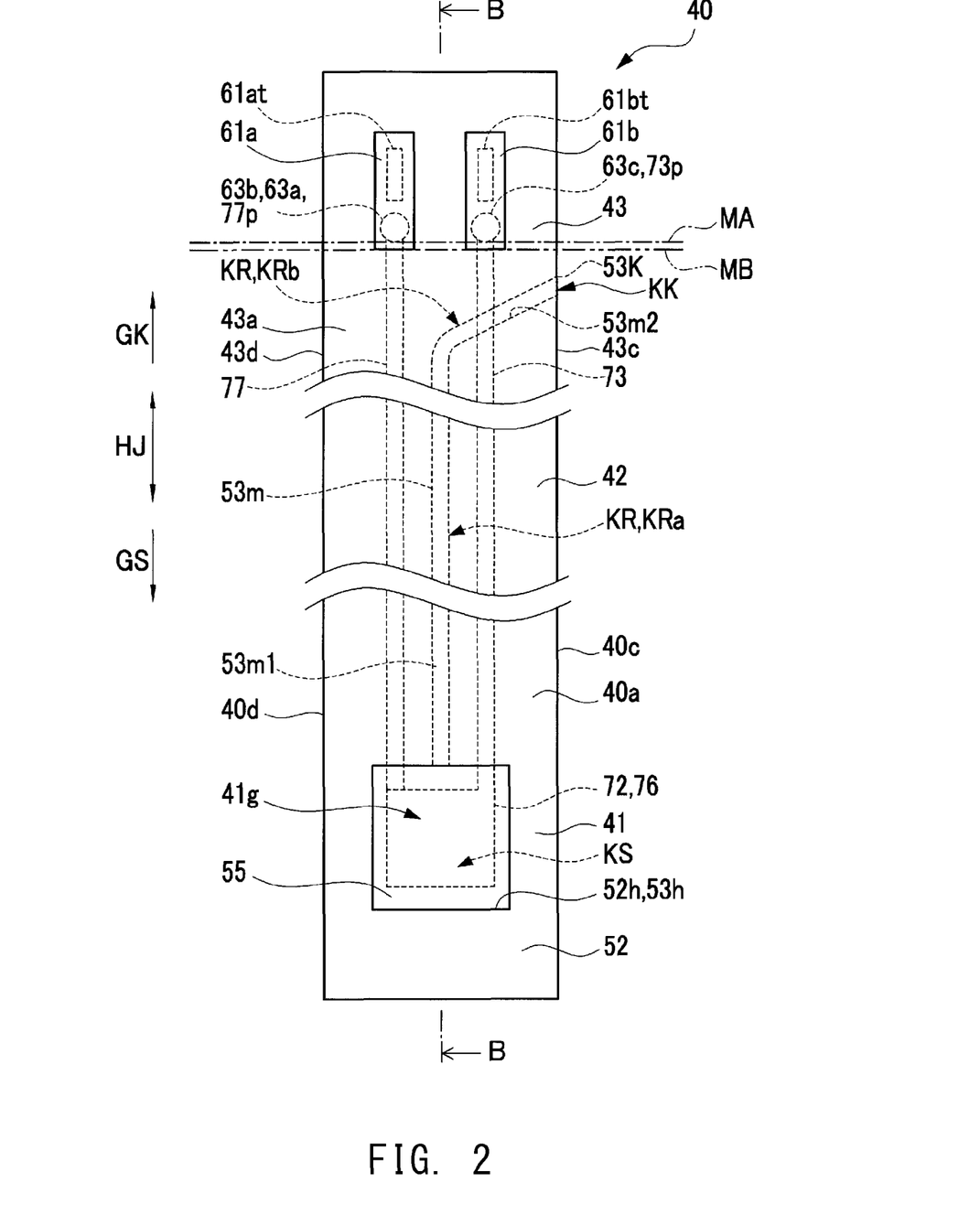
FIG. 2 is a plan view of a gas detection element according to the first embodiment as viewed from a first main surface side.

As will be described later, the entirety of the reference gas introduction passage KR is provided on the forward side GS with respect to the five through hole conductors 63a to 63e and the contact portions 61at, 61bt, 61ct, and 61dt of the four electrode pads 61a to 61d. Furthermore, the entirety of the reference gas introduction passage KR is provided on the forward side GS with respect to the electrode pads 61a to 61d and the through hole conductors 63a to 63e. In FIGS. 2 and 5, a first forward position MA indicated by the dash-dot line indicates the position in the axial direction HJ of the most forward one among the contact portions 61at to 61dt and the five through hole conductors 63a to 63e. Also, a second forward position MB indicated by the dash-dot-dot line indicates the position in the axial direction HJ of the most forward one among the electrode pads 61a to 61d and the through hole conductors 63a to 63e.

The entirety of the reference gas introduction passage KR is provided on the forward side GS with respect to the first forward position MA and the second forward position MB. Also, in the assembled gas sensor 1, the opening KK of the reference gas introduction passage KR is located on the forward side GS with respect to the insulating separator 85, which will be described later. As will be described later, the reference gas introduction passage KR extends in parallel with the first main surface 40a and the second main surface 40b of the gas detection element 40 without extending in the thickness direction TJ of the gas detection element 40 and opens at the first side surface 40c of the gas detection element 40 (the first side surface 43c of the element rear-end portion 43).

Next, the structure of the gas detection element 40 will be described in detail. The gas detection element 40 is configured such that a plurality of (specifically, four) ceramic layers (a solid electrolyte layer 51, a first insulating layer 52, a second insulating layer 53, and a third insulating layer 54) are laminated together in the thickness direction TJ (a direction orthogonal to the first main surface 40a and the second main surface 40b) (see FIGS. 3 to 5). The solid electrolyte layer 51 is a ceramic layer which contains zirconia as a main component and has oxygen ion conductivity. The solid electrolyte layer 51 has a tubular first through hole conductor 63a provided therethrough and formed at a predetermined position of a rear end portion which partially constitutes the element rear-end portion 43.

Figure 3:
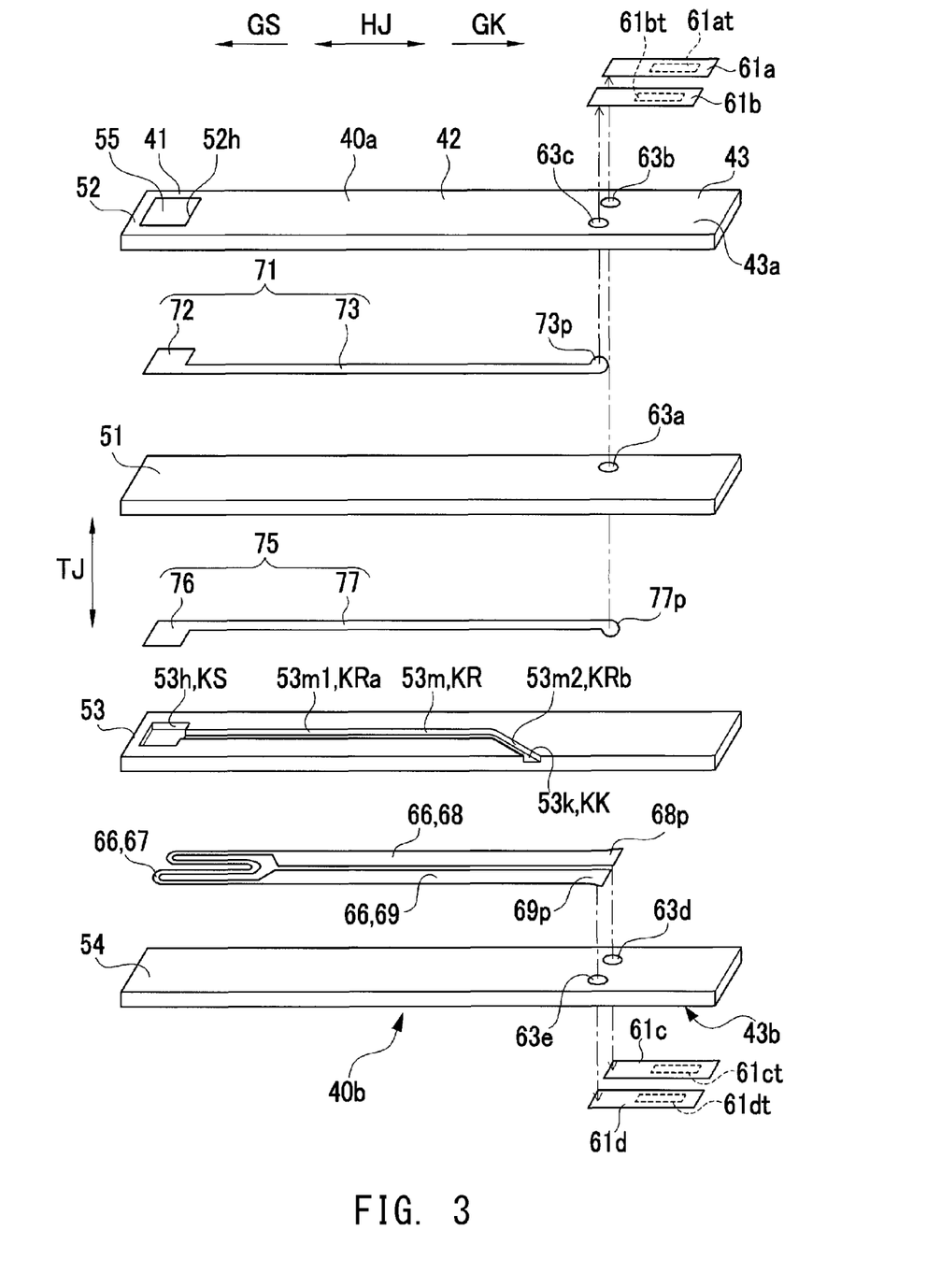
FIG. 3 is an exploded perspective view of the gas detection element according to the first embodiment.
Figure 4:
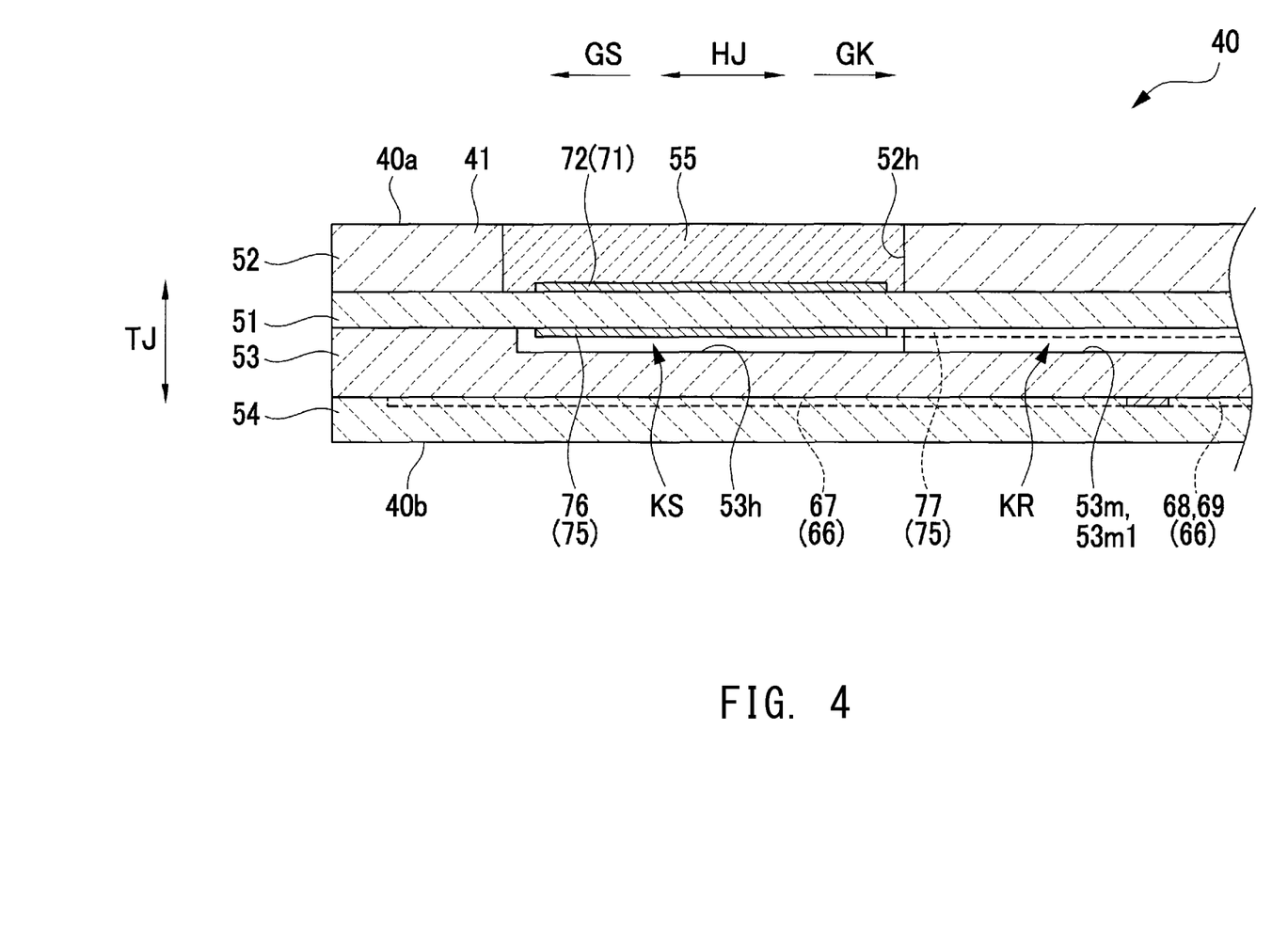
FIG. 4 is a sectional view of a forward end portion of the gas detection element according to the first embodiment, showing a portion of a sectional view taken along line B-B of FIG. 2.

The first insulating layer 52 located at an upper position in FIGS. 3 to 5 is a ceramic layer which is laminated on one main surface of the solid electrolyte layer 51 and contains alumina as a main component. The first insulating layer 52 has a gas introduction hole 52h having a rectangular shape as viewed in plane, adapted to introduce exhaust gas, provided therethrough, and formed at a forward end portion which partially constitutes the element forward-end portion 41. A porous, rectangular plate-like protection layer 55 is disposed in the gas introduction hole 52h for protecting a measuring electrode 72, which will be described later.

The aforementioned first electrode pad 61a and second electrode pad 61b are formed on the main surface of the first insulating layer 52 which corresponds to the first main surface 40a of the gas detection element 40, at predetermined positions on that rear end portion of the first insulating layer 52 which partially constitutes the element rear-end portion 43. Also, the first insulating layer 52 has a tubular second through hole conductor 63b and a tubular third through hole conductor 63c provided therethrough and formed at predetermined positions of the rear end portion which partially constitutes the element rear-end portion 43. The second through hole conductor 63b is connected at one end to the first through hole conductor 63a provided through the solid electrolyte layer 51 and is connected at the other end to the first electrode pad 61a formed on the first insulating layer 52. Also, the third through hole conductor 63c is connected to the second electrode pad 61b formed on the first insulating layer 52.

A first conductor 71 is composed of the measuring electrode 72 and a lead 73 and is formed on the solid electrolyte layer 51; i.e., between the solid electrolyte layer 51 and the first insulating layer 52. The measuring electrode 72 has a rectangular shape and faces the gas introduction hole 52h of the first insulating layer 52. The lead 73 extends from the measuring electrode 72 toward the rear side GK and is connected, at a rear-end pad portion 73p, to the third through hole conductor 63c provided through the first insulating layer 52. Thus, the measuring electrode 72 electrically communicates with the second electrode pad 61b through the lead 73 and the third through hole conductor 63c.

The second insulating layer 53 located below the solid electrolyte layer 51 in FIGS. 3 to 5 is a ceramic layer which is laminated on the other main surface of the solid electrolyte layer 51 and contains alumina as a main component. The second insulating layer 53 has a reference chamber recess 53h having a rectangular shape as viewed in plane and formed in a depressed manner at a side toward the solid electrolyte layer 51 at a forward end portion which partially constitutes the element forward-end portion 41. The reference chamber recess 53h is enclosed by the solid electrolyte layer 51 and the second insulating layer 53, thereby forming a reference chamber KS.

Also, the second insulating layer 53 has a reference gas introduction groove 53m formed at a side toward the solid electrolyte layer 51 and connected to the reference chamber recess 53h. The reference gas introduction groove 53m is enclosed by the solid electrolyte layer 51 and the second insulating layer 53, thereby forming the reference gas introduction passage KR. Specifically, the reference introduction groove 53m is composed of a first groove portion 53m1 and a second groove portion 53m2. The first groove portion 53m1 extends from the reference chamber recess 53h rectilinearly in the axial direction HJ (the longitudinal direction of the gas detection element 40; the vertical direction in FIG. 2; and the horizontal direction in FIGS. 3 to 5) between the element forward-end portion 41 and the element rear-end portion 43. The first groove portion 53m1 is enclosed by the solid electrolyte layer 51 and the second insulating layer 53, thereby forming a forward introduction portion KRa of the reference gas introduction passage KR.

The second groove portion 53m2 bends at the rear end of the first groove portion 53m1, extends obliquely toward the rear side GK, and opens at the first side surface 43c of the element rear-end portion 43. The second groove portion 53m2 is enclosed by the solid electrolyte layer 51 and the second insulating layer 53, thereby forming a bent introduction portion KRb of the reference gas introduction passage KR. An opening 53k at the rear end of the second groove portion 53m2 is enclosed by the solid electrolyte layer 51 and the second insulating layer 53, thereby forming the opening KK of the reference gas introduction passage KR.

By virtue of the thus-configured reference gas introduction passage KR, reference gas contained in the reference gas space RA (specifically, the air introduced into the reference gas space RA) to which the element rear-end portion 43 is exposed can be introduced into the reference chamber KS through the opening KK. The entirety of the reference gas introduction passage KR (the forward introduction portion KRa, the bent introduction portion KRb, and the opening KK) is provided on the forward side GS with respect to the contact portions 61at to 61dt of the four electrode pads 61a to 61d and the five through hole conductors 63a to 63e. Furthermore, the entirety of the reference gas introduction passage KR is provided on the forward side GS with respect to the electrode pads 61a to 61d and the through hole conductors 63a to 63e. Also, in the assembled gas sensor 1, the opening KK of the reference gas introduction passage KR is located on the forward side GS with respect to the insulating separator 85, which will be described later.

A second conductor 75 is composed of a reference electrode 76 and a lead 77 and is formed on the solid electrolyte layer 51; i.e., between the solid electrolyte layer 51 and the second insulating layer 53. The reference electrode 76 has a rectangular shape and faces the measuring electrode 72 with the solid electrolyte layer 51 intervening therebetween. The lead 77 extends from the reference electrode 76 toward the rear side GK and is connected, at a rear-end pad portion 77p, to the first through hole conductor 63a provided through the solid electrolyte layer 51. Thus, the reference electrode 76 electrically communicates with the first electrode pad 61a through the lead 77, the first through hole conductor 63a, and the second through hole conductor 63b. The aforementioned detecting section 41g of the gas detection element 40 is composed of the measuring electrode 72 and the reference electrode 76 which face each other with the solid electrolyte layer 51 intervening therebetween, the gas introduction hole 52h and the protection layer 55 which the measuring electrode 72 faces, and the reference chamber KS which the reference electrode 76 faces.

The third insulating layer 54 located below the second insulating layer 53 in FIGS. 3 to 5 is a ceramic layer which is laminated on the second insulating layer 53 and contains alumina as a main component. The aforementioned third electrode pad 61c and fourth electrode pad 61d are formed on the main surface of the third insulating layer 54 which corresponds to the second main surface 40b of the gas detection element 40, at predetermined positions on that rear end portion of the third insulating layer 54 which partially constitutes the element rear-end portion 43. Also, the third insulating layer 54 has a tubular fourth through hole conductor 63d and a tubular fifth through hole conductor 63e provided therethrough and formed at predetermined positions of the rear end portion which partially constitutes the element rear-end portion 43. The fourth through hole conductor 63d is connected to the third electrode pad 61c formed on the third insulating layer 54. The fifth through hole conductor 63e is connected to the fourth electrode pad 61d formed on the third insulating layer 54.

A third conductor 66 is composed of a heat-generating resistor 67 and two leads 68 and 69 and is formed between the second insulating layer 53 and the third insulating layer 54. The heat-generating resistor 67 has a meandering form and is disposed within the element forward-end portion 41. The two leads 68 and 69 extend toward the rear side GK from respective opposite ends of the heat-generating resistor 67. The lead 68 is connected, at a rear-end pad portion 68p, to the fourth through hole conductor 63d provided through the third insulating layer 54. Thus, one end of the heat-generating resistor 67 electrically communicates with the third electrode pad 61c through the lead 68 and the fourth through hole conductor 63d. The other lead 69 is connected, at a rear-end pad portion 69p, to the fifth through hole conductor 63e provided through the third insulating layer 54. Thus, the other end of the heat-generating resistor 67 electrically communicates with the fourth electrode pad 61d through the lead 69 and the fifth through hole conductor 63e.

In the gas detection element 40 described above, reference gas (specifically, the air introduced into the reference gas space RA) existing around the element rear-end portion 43 and having a fixed oxygen concentration is introduced into the reference chamber KS through the reference gas introduction passage KR having the opening KK at the first side surface 43c of the element rear-end portion 43. Meanwhile, exhaust gas existing around the element forward-end portion 41 is introduced into the gas introduction hole 52h (protection layer 55) of the first insulating layer 52 through the protection layer 45. Thus, the measuring electrode 72, the reference electrode 76, and the solid electrolyte layer 51 sandwiched therebetween constitute an oxygen concentration cell, which generates voltage in response to the concentration of oxygen contained in exhaust gas in contact with the measuring electrode 72. Therefore, by measuring the voltage, the oxygen concentration of exhaust gas can be detected.

Next, the insulating separator 85 and the terminal members 80 will be described (see FIG. 1). The insulating separator 85 is formed of an insulating ceramic (specifically, alumina); is disposed in the outer tube 30 away, in the axial direction HJ, from the metallic shell 10 and the sleeve 95; and accommodates a portion of the element rear-end portion 43 of the gas detection element 40 and four terminal members 80 in its accommodating portions 85h, respectively. The insulating separator 85 holds the terminal members 80 in a mutually noncontact and insulated condition.

The insulating separator 85 is composed of a forward separator 86 located on the forward side GS and a rear separator 87 located on the rear side GK with respect to the forward separator 86. Within the forward separator 86, forward contact portions 81 of the four terminal members 80 are disposed away from one another in a mutually insulated manner, and the element rear-end portion 43 is disposed radially inward of the forward contact portions 81. The forward contact portions 81 of the terminal members 80 are in contact with the contact portions 61at to 61dt of the electrode pads 61a to 61d, respectively, thereby establishing electrical communication.

Within the rear separator 87, rear-end crimp portions 82 of the four terminal members 80 are inserted. The rear-end crimp portions 82 are crimped to the lead wires 83 (core wires thereof), respectively. The lead wires 83 extend toward the rear side GK beyond the rear separator 87 and further extend through the respective second through holes 35h2 of the elastic member 35, thereby extending outward from the gas sensor 1. The tubular metal holding member 88 is bent radially inward at its rear side GK and disposed between the insulating separator 85 and the outer tube 30. The metal holding member 88 grips the insulating separator 85 from radially outside, whereby the insulating separator 85 is held to the outer tube 30.

As described above, in the gas sensor 1, the entirety of the reference gas introduction passage KR is provided in the gas detection element 40 on the forward side GS with respect to the contact portions 61at to 61dt of the four electrode pads 61a to 61d and the five through hole conductors 63a to 63e; specifically, on the forward side GS with respect to the first forward position MA which corresponds to the forward ends of the through hole conductors 63a to 63e. Thus, reference gas can be reliably introduced to the detecting section 41g. Additionally, there can be prevented deterioration in strength of that region of the element rear-end portion 43 in which the through hole conductors 63a to 63e and the contact portions 61at to 61dt of the electrode pads 61a to 61d are provided, which could otherwise result from existence of the reference gas introduction passage KR.

Furthermore, in the present first embodiment, the entirety of the reference gas introduction passage KR is provided in the gas detection element 40 on the forward side GS with respect to the electrode pads 61a to 61d (including the contact portions 61at to 61dt) and the through hole conductors 63a to 63e; specifically, on the forward side GS with respect to the second forward position MB which corresponds to the forward ends of the electrode pads 61a to 61d. Thus, although the gas detection element 40 has the reference gas introduction passage KR, that region of the element rear-end portion 43 in which the electrode pads 61a to 61d and the through hole conductors 63a to 63e are provided can reliably maintain high strength. Accordingly, use of the gas detection element 40 enhances the reliability of the gas sensor 1.

Furthermore, in the present first embodiment, the opening KK of the reference gas introduction passage KR is provided in the gas detection element 40 on the forward side GS with respect to the insulating separator 85 rather than within the accommodating portions 85h of the insulating separator 85. Thus, reference gas can be more reliably introduced from the opening KK.

Also, in the present first embodiment, the entirety of the reference gas introduction passage KR is provided along the single solid electrolyte layer 51, which partially constitutes the gas detection element 40, without the reference gas introduction passage KR extending in the thickness direction TJ of the gas detection element 40, and the opening KK is provided at the first side surface 43c of the element rear-end portion 43. In this manner, the reference gas introduction passage KR assumes a two-dimensionally extending form rather than a three-dimensionally extending form, whereby the reference gas introduction passage KR can be formed easily and reliably; thus, the gas sensors 1 can be manufactured inexpensively with small variations in characteristics.

B. Second Embodiment

Figure 6:
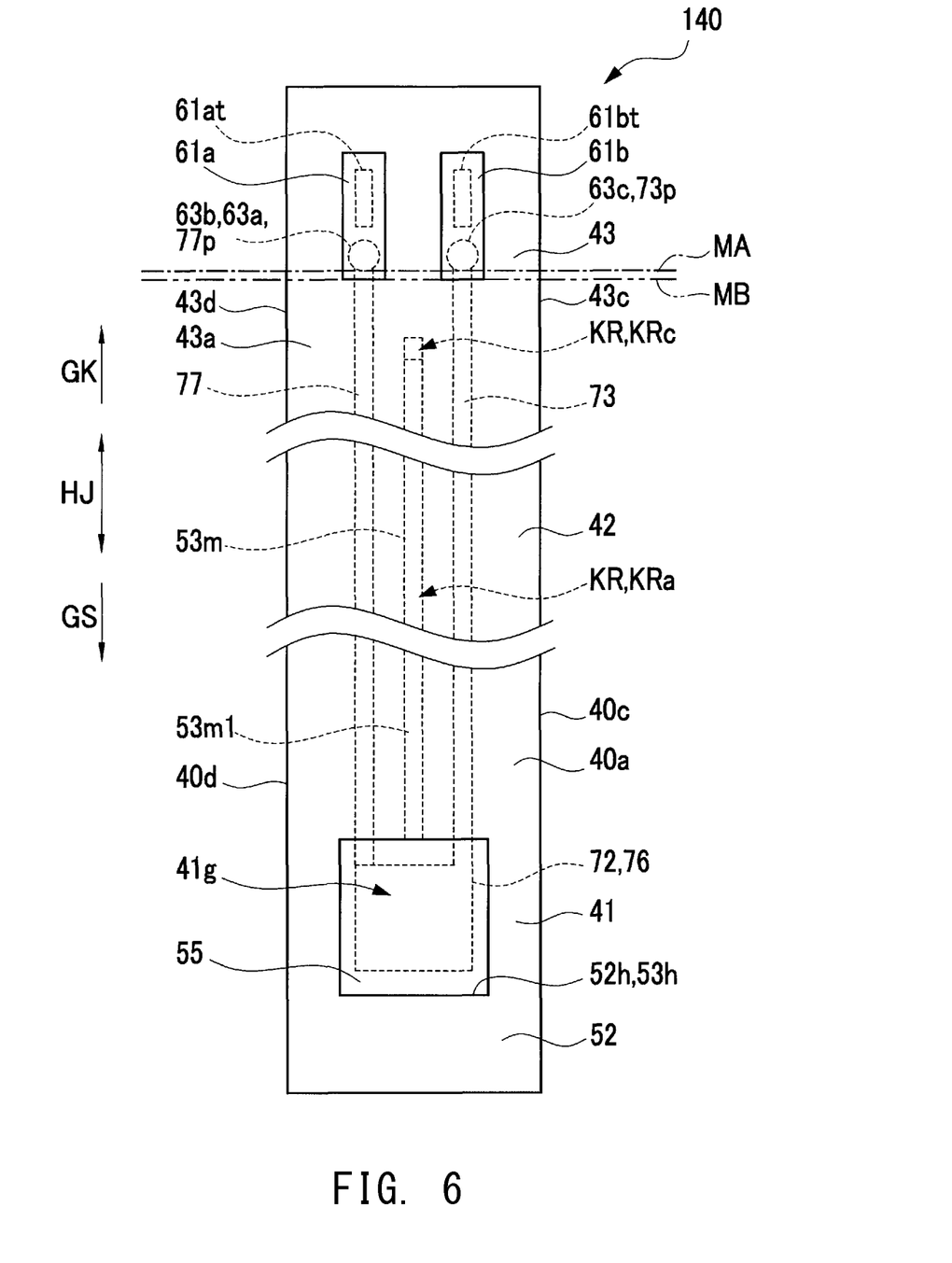
FIG. 6 is a plan view of a gas detection element according to embodiment 2 of the present invention as viewed from a first main surface side.
Figure 7:
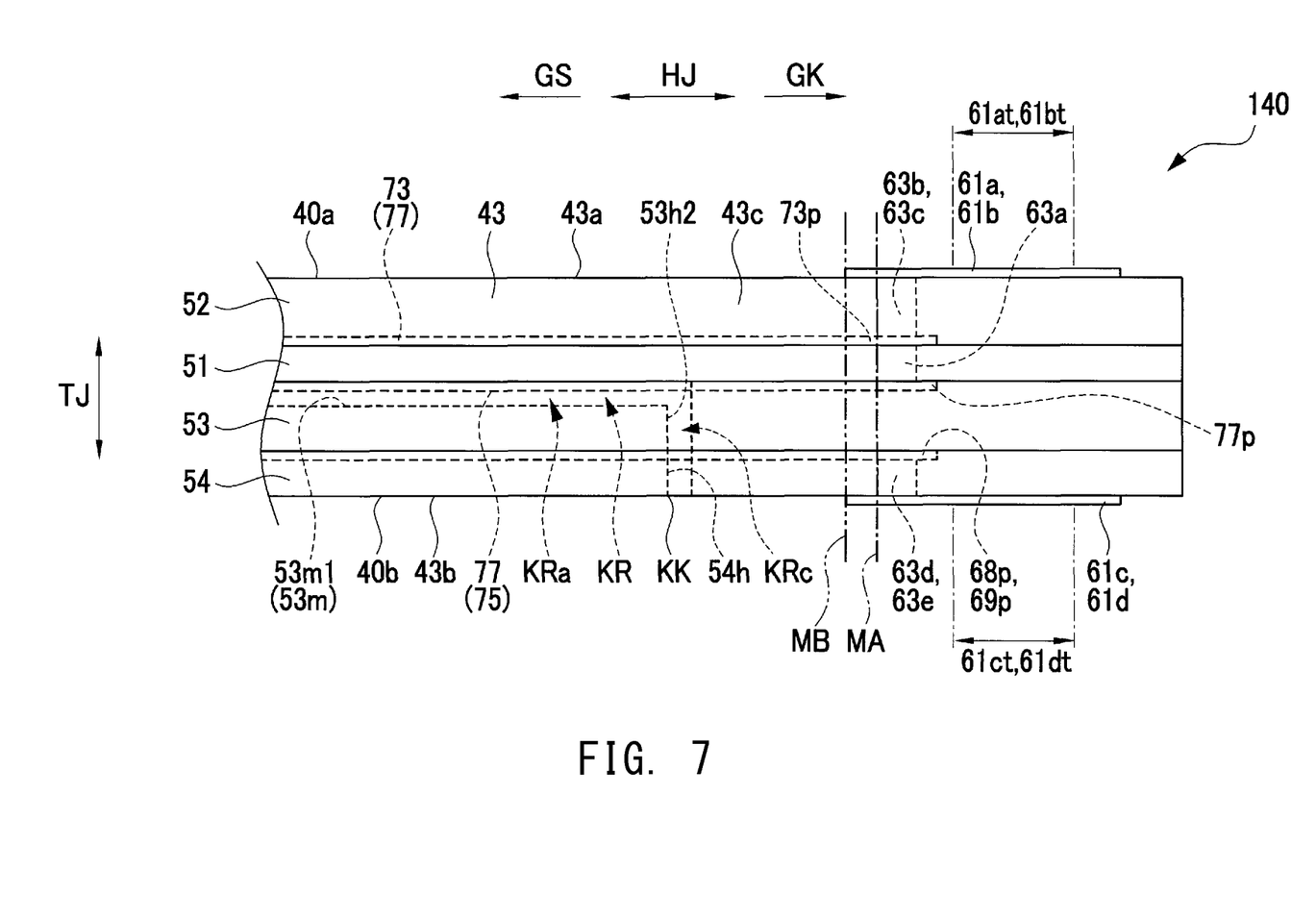
FIG. 7 is a side view of a rear end portion of the gas detection element according to embodiment 2 as viewed from a first side surface side.

Next, a second embodiment of the present invention will be described (see FIGS. 6 and 7). A gas sensor 101 according to the second embodiment is similar to the gas sensor 1 according to the first embodiment except that the reference gas introduction passage KR provided in a gas detection element 140 differs from that provided in the gas detection element 40. In FIGS. 6 and 7, structural features basically similar to those in the first embodiment are denoted by the same reference numerals as those of the first embodiment.

In the second embodiment also, the second insulating layer 53 has, at a side toward the solid electrolyte layer 51, the reference chamber recess 53h and the reference gas introduction groove 53m connected to the reference chamber recess 53h. However, the reference gas introduction groove 53m is composed of only the aforementioned first groove portion 53m1 which extends rectilinearly from the reference chamber recess 53h toward the rear side GK. The reference gas introduction groove 53m (first groove portion 53m1) is enclosed by the solid electrolyte layer 51 and the second insulating layer 53, thereby forming the forward introduction portion KRa of the reference gas introduction passage KR.

In the present second embodiment, the second groove portion 53m2 of the first embodiment is replaced with a through hole 53h2 which is provided through the second insulating layer 53 and connected to the rear end of the first groove portion 53m1 at that rear end portion of the second insulating layer 53 which partially constitutes the element rear-end portion 43. Furthermore, the third insulating layer 54 has a through hole 54h provided therethrough at a rear end portion which partially constitutes the element rear-end portion 43, in such a manner as to communicate with the through hole 53h2 of the second insulating layer 53. In the present second embodiment, the through holes 53h2 and 54h constitute a through introduction portion KRc of the reference gas introduction passage KR. An opening of the through hole 54h which opens at the second main surface 43b of the element rear-end portion 43 is the opening KK of the reference gas introduction passage KR.

The entirety of the reference gas introduction passage KR (the forward introduction portion KRa, the through introduction portion KRc, and the opening KK) is also provided on the forward side GS with respect to the contact portions 61at to 61dt of the four electrode pads 61a to 61d and the five through hole conductors 63a to 63e; specifically, on the forward side GS with respect to the first forward position MA which is indicated by the dash-dot line in FIGS. 6 and 7 and corresponds to the forward ends of the through hole conductors 63a to 63e. Thus, reference gas can be reliably introduced to the detecting section 41g. Additionally, there can be prevented deterioration in strength of that region of the element rear-end portion 43 in which the through hole conductors 63a to 63e and the contact portions 61at to 61dt of the electrode pads 61a to 61d are provided, which could otherwise result from existence of the reference gas introduction passage KR.

Furthermore, in the present second embodiment also, the entirety of the reference gas introduction passage KR is provided on the forward side GS with respect to the electrode pads 61a to 61d and the through hole conductors 63a to 63e; specifically, on the forward side GS with respect to the second forward position MB which is indicated by the dash-dot-dot line in FIGS. 6 and 7 and corresponds to the forward ends of the electrode pads 61a to 61d. Thus, although the gas detection element 40 has the reference gas introduction passage KR, that region of the element rear-end portion 43 in which the electrode pads 61a to 61d and the through hole conductors 63a to 63e are provided can reliably maintain high strength. Accordingly, use of the gas detection element 140 enhances the reliability of the gas sensor 101. Furthermore, in the present second embodiment also, the opening KK of the reference gas introduction passage KR is provided in the gas detection element 40 on the forward side GS with respect to the insulating separator 85. Thus, reference gas can be more reliably introduced from the opening KK. Other structural features similar to those of the first embodiment yield actions and effects similar to those yielded by the first embodiment.

While the present invention has been described with reference to the first and second embodiments described above, the present invention is not limited thereto, but may be modified as appropriate without departing from the gist of the invention.

For example, in the first and second embodiments, the present invention is applied to a gas sensor having a gas detection element in which a single oxygen concentration cell is formed; i.e., a gas sensor having a so-called one-cell type gas detection element. However, the present invention is not limited thereto. The present invention can also be applied to a gas sensor having a gas detection element in which a plurality of oxygen concentration cells are formed, such as a two-cell type or three-cell type gas detection element, so long as the gas detection element has the reference gas introduction passage formed therein.

DESCRIPTION OF REFERENCE NUMERALS

1, 101: gas sensor
10: metallic shell
10h: axial hole
20: protector
30: outer tube
40, 140: gas detection element
41: element forward-end portion
41g: detecting section
43: element rear-end portion
43a: first main surface (radially outer perimetric surface) (of element rear-end portion)
43b: second main surface (radially outer perimetric surface) (of element rear-end portion)
43c: first side surface (radially outer perimetric surface) (of element rear-end portion)
43d: second side surface (radially outer perimetric surface) (of element rear-end portion)
51: solid electrolyte layer (ceramic layer)
52: first insulating layer (ceramic layer)
53: second insulating layer (ceramic layer)
54: third insulating layer (ceramic layer)
61a: first electrode pad
61at: contact portion (of first electrode pad)
61b: second electrode pad
61bt: contact portion (of second electrode pad)
61c: third electrode pad
61ct: contact portion (of third electrode pad)
61d: fourth electrode pad
61dt: contact portion (of fourth electrode pad)
63a: first through hole conductor
63b: second through hole conductor
63c: third through hole conductor
63d: fourth through hole conductor
63e: fifth through hole conductor
80: terminal member
85: insulating separator
85h: accommodating portion
91: metal cup (holding member)
92: ceramic ring (holding member)

93: first talc ring (holding member)
94: second talc ring (holding member)
95: sleeve (holding member)
AX: axial line
HJ: axial direction
GS: forward side (in axial direction)
GK: rear side (in axial direction)
KR: reference gas introduction passage
KK: opening
RA: reference gas space
MA: first forward position
MB: second forward position

What is claimed is:

1. A gas sensor comprising:
   a tubular metallic shell having an axial hole extending therethrough in an axial direction;
   a holding member disposed in the axial hole of the metallic shell;
   a gas detection element held by the holding member in the axial hole of the metallic shell, the gas detection element having a plate-like form extending in the axial direction and including:
      an element forward-end portion located on a forward side in the axial direction with respect to the holding member and including a detecting section for detecting a particular gas component contained in gas to be measured, and
      an element rear-end portion located on a rear side in the axial direction with respect to the holding member, exposed to reference gas, and including an electrode pad having a contact portion, and a through hole conductor in electrical communication with the electrode pad; and
   a terminal member in contact with the contact portion of the electrode pad;
   wherein:
      the element rear-end portion further includes a radially outer perimetric surface which defines an opening, and the gas detection element defines a reference gas introduction passage extending from the opening to the detecting section for introducing the reference gas to the detecting section, and
      the entirety of the reference gas introduction passage is on the forward side in the axial direction with respect to the through hole conductor and the contact portion of the electrode pad.

2. A gas sensor according to claim 1, wherein the entirety of the reference gas introduction passage is provided on the forward side in the axial direction with respect to the electrode pad and the through hole conductor.

3. A gas sensor according to claim 1, further comprising an insulating separator which accommodates the terminal member and partially accommodates the element rear-end portion of the gas detection element,
   wherein the insulating separator is disposed away from the holding member and the metallic shell, and
   the opening of the reference gas introduction passage is provided on the forward side in the axial direction with respect to the insulating separator.

4. A gas sensor according to claim 1, wherein
   the gas detection element includes a plurality of ceramic layers laminated in a thickness direction;
   the radially outer perimetric surface comprises a pair of main surfaces which face each other in the thickness direction, and side surfaces which connect the pair of main surfaces to each other; and
   the reference gas introduction passage is along one of the plurality of ceramic layers, and the opening is at one of the side surfaces.

5. A gas detection element having a plate-like form extending in an axial direction, and comprising:
   an element forward-end portion located on a forward side in the axial direction and including a detecting section for detecting a particular gas component in gas to be measured; and
   an element rear-end portion located on a rear side in the axial direction including an electrode pad having a contact portion with which a terminal member comes into contact, a through hole conductor in electrical communication with the electrode pad, and a radially outer perimetric surface defining an opening;
   the gas detection element defining a reference gas introduction passage extending from the opening to the detecting section for introducing reference gas to the detecting section;
   wherein the entirety of the reference gas introduction passage is on the forward side in the axial direction with respect to the through hole conductor and the contact portion of the electrode pad.

6. A gas detection element having a plate-like form extending in an axial direction, and comprising:
   an element forward-end portion located on a forward side in the axial direction and including a detecting section for detecting a particular gas component in gas to be measured; and
   an element rear-end portion located on a rear side in the axial direction including an electrode pad, a through hole conductor in electrical communication with the electrode pad, and a radially outer perimetric surface defining an opening;
   the gas detection element defining a reference gas introduction passage extending from the opening to the detecting section for introducing reference gas to the detecting section;
   wherein the entirety of the reference gas introduction passage is provided on the forward side in the axial direction with respect to the electrode pad and the through hole conductor.

7. A gas detection element according to claim 5, further comprising a plurality of ceramic layers laminated in a thickness direction,
   wherein the radially outer perimetric surface includes a pair of main surfaces which face each other in the thickness direction, and side surfaces which connect the pair of main surfaces to each other, and
   the reference gas introduction passage is along one of the ceramic layers, and the opening is at one of the side surfaces.

8. A gas detection element according to claim 6, further comprising a plurality of ceramic layers laminated in a thickness direction,
   wherein the radially outer perimetric surface includes a pair of main surfaces which face each other in the thickness direction, and side surfaces which connect the pair of main surfaces to each other, and
   the reference gas introduction passage is along one of the ceramic layers, and the opening is at one of the side surfaces.

* * * * *